United States Patent
Vasconcelos (10) Patent No.: US 11,638,802 B2
(45) Date of Patent: May 2, 2023

(54) CHILLED-AIR INHALER DEVICE AND METHODS OF USING A CHILLED-AIR INHALER DEVICE FOR THE ALLEVIATION OF RESPIRATORY SYMPTOMS

(71) Applicant: David Vasconcelos, Dartmouth, MA (US)

(72) Inventor: David Vasconcelos, Dartmouth, MA (US)

(73) Assignee: David Vasconcelos, Dartmouth, MA (US)

( * ) Notice: Subject to any disclaimer, the term of this patent is extended or adjusted under 35 U.S.C. 154(b) by 572 days.

(21) Appl. No.: 16/777,621

(22) Filed: Jan. 30, 2020

(65) Prior Publication Data

US 2020/0238040 A1 Jul. 30, 2020

Related U.S. Application Data

(60) Provisional application No. 62/798,675, filed on Jan. 30, 2019.

(51) Int. Cl.
*A61M 16/10* (2006.01)
*A61M 16/04* (2006.01)
*A61F 7/12* (2006.01)
*A61F 7/00* (2006.01)
(Continued)

(52) U.S. Cl.
CPC ....... *A61M 16/1075* (2013.01); *A61F 7/0085* (2013.01); *A61F 7/12* (2013.01); *A61M 16/0488* (2013.01); *A61F 2007/006* (2013.01); *A61F 2007/0063* (2013.01); *A61M 16/0066* (2013.01); *A61M 16/14* (2013.01); *A61M 2205/3606* (2013.01)

(58) Field of Classification Search
CPC ............ A61M 16/075; A61M 16/0488; A61M 2205/3606; A61M 2205/3646; A62B 9/003; A61F 7/12; A61F 7/0085; A61F 2007/006; A61F 2007/0063
See application file for complete search history.

(56) References Cited

U.S. PATENT DOCUMENTS 3,140,590 A * 7/1964 Gleockler .............. A62B 9/003
62/421
3,908,649 A 9/1975 Eckstein
(Continued)

FOREIGN PATENT DOCUMENTS

EP 2599514 6/2013
GB 327081 3/1930

*Primary Examiner* — Colin W Stuart
*Assistant Examiner* — Douglas Y Sul
(74) *Attorney, Agent, or Firm* — Caldwell Intellectual Property Law (57) ABSTRACT

A chilled-air inhaler device for the alleviation of respiratory symptoms includes a body containing a hollow chamber through which air is forced or drawn past at least an air-chilling surface. In an embodiment the air-chilling surface may include water ice. Connected to the body and hollow chamber at one end is a mouthpiece including an opening that connects from environmental air outside of the hollow chamber to the hollow chamber. Connected to the hollow chamber at a second end is an inlet which connects to a source of air. In an embodiment, the inlet may connect to an external device such blower or nebulizer.

19 Claims, 3 Drawing Sheets

(51) Int. Cl.
*A61M 16/14* (2006.01)
*A61M 16/00* (2006.01)

(56) References Cited

U.S. PATENT DOCUMENTS

| | | | | |
|---|---|---|---|---|
| 5,146,757 | A | * | 9/1992 | Dearing ................. A42B 3/285 62/61 |
| 5,542,413 | A | * | 8/1996 | Horn ...................... A62B 9/003 128/204.15 |
| 5,562,644 | A | * | 10/1996 | McLeod ............... A61F 7/0085 604/291 |
| 6,997,184 | B2 | | 2/2006 | Donohue |
| 8,776,789 | B2 | | 7/2014 | McCabe |
| 9,004,065 | B2 | | 4/2015 | Vervoort |
| 9,272,103 | B2 | | 3/2016 | Storz |
| 10,039,895 | B2 | | 8/2018 | Hoke-Kearns et al. |
| 2005/0229930 | A1 | * | 10/2005 | Donohue .......... A61M 16/1075 128/204.15 |
| 2009/0056716 | A1 | * | 3/2009 | Newman, Jr. ..... A61M 16/0858 128/204.18 |
| 2009/0229609 | A1 | * | 9/2009 | Carrier ................. A61M 15/00 128/204.15 |
| 2011/0005522 | A1 | * | 1/2011 | Vervoort ............... A61M 16/16 128/203.14 |
| 2011/0180069 | A1 | * | 7/2011 | McCabe ............... F24F 5/0017 128/204.15 |
| 2012/0125335 | A1 | | 5/2012 | Affinito |
| 2012/0167878 | A1 | * | 7/2012 | Belson ................. A61M 16/12 128/200.14 |
| 2013/0312749 | A1 | | 11/2013 | Bornn et al. |
| 2016/0022933 | A1 | * | 1/2016 | Ciancone .......... A61M 15/0086 128/200.23 |
| 2016/0199673 | A1 | | 7/2016 | Berkson |
| 2019/0290880 | A1 | * | 9/2019 | Dickson, Jr. ...... A61M 16/0816 |

\* cited by examiner

CHILLED-AIR INHALER DEVICE AND METHODS OF USING A CHILLED-AIR INHALER DEVICE FOR THE ALLEVIATION OF RESPIRATORY SYMPTOMS

CROSS-REFERENCE TO RELATED APPLICATIONS

This application claims the benefit of priority of U.S. Provisional Patent Application Ser. No. 62/798,675, filed on Jan. 30, 2019, and titled "A CHILLED-AIR INHALER DEVICE AND METHODS OF USING A CHILLED-AIR INHALER DEVICE FOR THE ALLEVIATION OF RESPIRATORY SYMPTOMS," which is incorporated by reference herein in its entirety.

FIELD OF THE INVENTION

The present invention generally relates to the field of breathing control devices. In particular, the present invention is directed to a chilled-air inhaler device and methods of using a chilled-air inhaler device for the alleviation of respiratory symptoms.

BACKGROUND

Respiratory symptoms such as bronchitis, asthma, wheezing, and/or croup commonly plague both the young and old alike. Current treatment for such conditions typically includes steroids which can present very serious side effects such as a racing heart and/or palpitation due to the stimulatory effects of such treatments. Furthermore, such treatments can be potentially cost-prohibitive to use, as they may require prior authorizations or even outright denials by insurance companies. This has hampered the use of such treatments and left many suffering from such serious conditions without adequate help.

SUMMARY OF THE DISCLOSURE

In one aspect, a chilled-air inhaler device for the alleviation of respiratory symptoms includes a body. The body includes a hollow chamber. The hollow chamber has a first end and a second end, and the hollow chamber has an interior space containing at least an air-chilling surface. The chilled-air inhaler device includes a mouthpiece connected to the body. The mouthpiece further comprises a mouthpiece opening connected to the second end of the hollow chamber. The mouthpiece opening connects the interior space of the hollow chamber to environmental air located outside of the hollow chamber. The chilled-air inhaler device includes an inlet including an inlet opening located at the first end of the hollow chamber, wherein the inlet opening connects the interior space of the hollow chamber to a source of air.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to devices and methods for the alleviation of respiratory symptoms. In an embodiment, a chilled-air inhaler device may be utilized to control respiratory symptoms such as bronchitis, asthma, wheezing, bronchiolitis, croup, and/or reducing inflammation in lungs using air-chilling equipment commonly found around one's home. Chilled-air inhaler device may be used for therapeutic uses such as meditation and relaxation, for addiction relief, and/or for calming effects from stress, anxiety, depression and/or post-traumatic stress disorder (PTSD). In an embodiment, chilled-air inhaler device may be utilized to relieve pain from smoke inhalation. Chilled-air inhaler device may freshen a user's breath and may have antimicrobial and/or dental implications. In an embodiment, chilled-air inhaler device may be used by persons including the very young and the very old without administering medications that may cause serious side effects or be contraindicated in such populations. Chilled air inhaler device may combine with or include a nebulizer or blower. Ease of use and economic functionality of chilled-air inhaler device make it a practical solution to many common disease states and habits.

Figure 1:
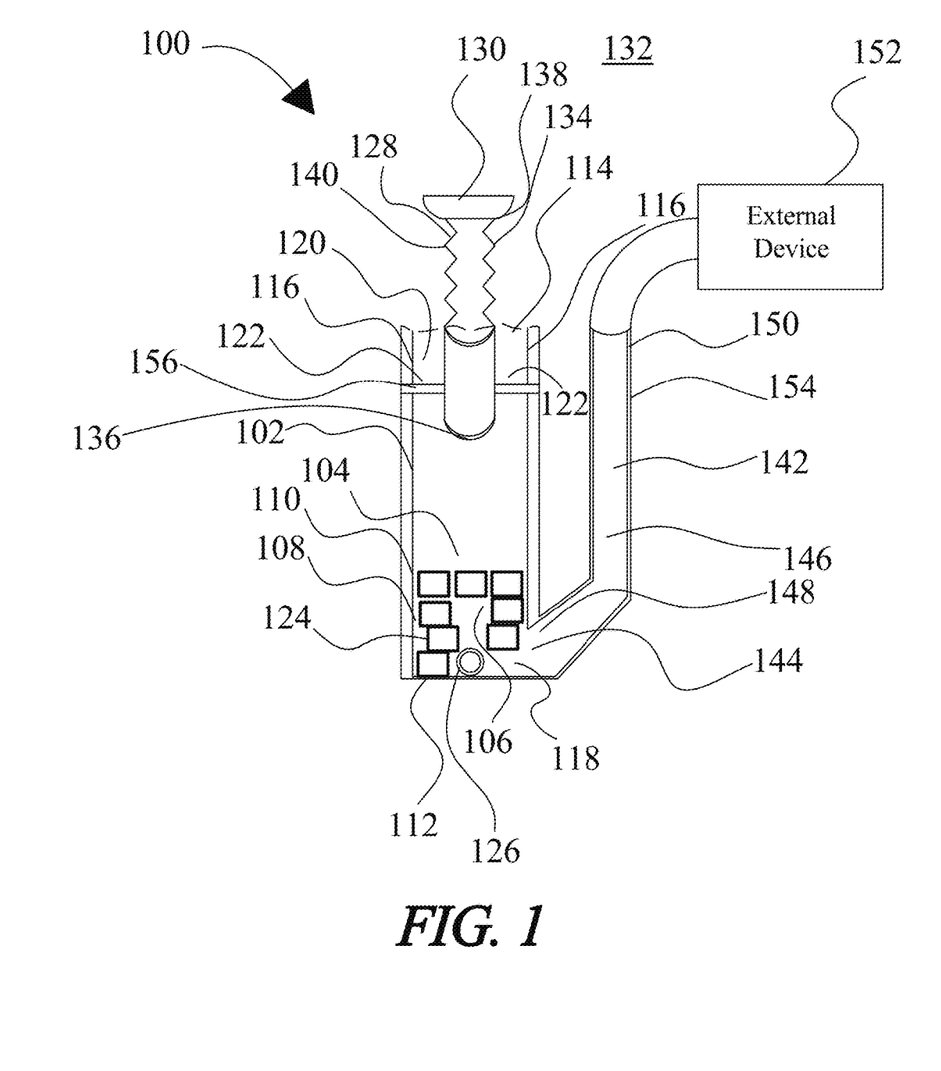
FIG. 1 illustrates a schematic drawing of a chilled-air inhaler device for the alleviation of respiratory symptoms.

Referring now to FIG. 1, a schematic drawing of an exemplary embodiment 100 of a chilled-air inhaler device for the alleviation of respiratory symptoms is illustrated. Chilled-air inhaler device includes a body 102 having a hollow chamber 104. Body 102 may form a structure for enclosing hollow chamber 104 containing at least an air-chilling surface 106. Body 102 may have any suitable shape, including any combination of curved, planar, or polyhedral surfaces. Body 102 may include a flat base, one or more feet extending from the body 102 to support it in a given configuration on a flat surface, or the like. As a non-limiting example, body 102 may have a cylindrical shape having a length and diameter sized to enclose hollow chamber 104. As a further non-limiting example, body 102 may have an ellipsoid shape having a length and diameter sized to enclose hollow chamber. Body 102 may have a substantially polyhedral shape, such as without limitation a rectilinear prism with rounded corners. Body 102 may include an interior 108 and exterior surface 110. In an embodiment, exterior surface 110 may contain at least a connection point that may allow for a cord to pass through at least a connection point thereby creating a lanyard. A lanyard may be hung around a user's neck for example, so that chilled-air inhaler device 100 may be hands free and/or more easily portable. Body may include a body first end 112, body second end 114. Body may include one or more body sides 116 connecting first end to second end; the body sides 116 may include one or more pairs of sides opposite each other on body, including without limitation one or more pairs of parallel sides. In an embodiment, body first end 112 may be equal in length and diameter size to body second end 114; alternatively, cross-sectional length and/or diameter may vary along the length of body 102. In an embodiment, body sides 116 may be equal to each other in length, widths, and/or diameters, or may have varying lengths, widths, and/or diameters. In yet another non-limiting example, body sides 116 may be equal in length, width, and/or diameter to body first end 112 and/or body second end 114.

Still referring to FIG. 1, body 102 and/or hollow chamber 104 may be composed of any suitable material and/or combination of materials. For instance, and without limitation, body may be composed at least in part of ethylene-vinyl acetate (EVA), thermoplastic, rubber, plastic, polyurethane, laminated thermoplastic, nylon, polyurethane, polyethylene, polyvinyl chloride (PVC), rubber, plastic, glass, polystyrene, polypropylene, metal, and/or aluminum. Body and/or hollow chamber may be manufactured and/or assembled according to any suitable process including without limitation molding processes such as injection molding, blow molding, or the like, subtractive processes such as machining, additive processes such as rapid prototyping, stereolithography, or the like, and/or extrusion-based processes. Persons skilled in the art, upon reviewing the entirety of this disclosure, will be aware of various materials and/or manufacturing processes suitable for producing body 102 and/or hollow chamber 104.

With continued reference to FIG. 1, hollow chamber 104 may include an empty space and/or cavity located inside of body 102. Hollow chamber 104 may have any three-dimensional and/or cross-sectional form suitable for body 102; hollow chamber 104 may have a similar form to body 102 or a distinct form from body 102. As a non-limiting example, hollow chamber 104 may have a cylindrical shape having a length and diameter sized to enclose an air-chilling surface. Hollow chamber may include a hollow chamber first end 118 and a hollow chamber second end 120. Hollow chamber may include one or more hollow chamber sides 122 connecting first end to second end; hollow chamber sides 122 may include one or more pairs of opposite or parallel sides. In an embodiment, hollow chamber first end 118 may be equal in length, width, and/or diameter to hollow chamber second end 120; hollow chamber 104 may have a cross-sectional area that varies over the length of hollow chamber. In an embodiment, hollow chamber sides 122 may be equal to each other in length, width and/or diameter; alternatively, hollow chamber opposite sides may vary from one another in size or shape. In yet another non-limiting example, hollow chamber opposite sides 122 may be equal in length, width, and/or diameter to hollow chamber first end 118 and/or hollow chamber second end 120. Body 102 length, width, and/or diameter may be equal to hollow chamber 104 length and diameter.

With continued reference to FIG. 1, hollow chamber 104 contains an interior space containing at least an air-chilling surface 106. Air-chilling surface 106 may include a surface that causes a reduction in temperature in air flowing over, past, and/or around it to generate chilled air. In an embodiment, air-chilling surface may cause a reduction in temperature between 40° to 60° Fahrenheit (4.4° to 15.5° Celsius). Air-chilling surface 106 may include a chilled air-permeable filling 124, which may include a filling that allows air to flow through the filling from hollow chamber first end 118 to hollow chamber second end 120. Chilled air-permeable filling may include, as a non-limiting example, ice, such as water ice, metal ice cubes, ice shavings, dry ice, and/or any type of thermal material. Chilled air-permeable filling 124 may include flavored chilled air. For example, water ice may contain flavors added to water and then frozen as flavored water ice. Flavors may include for example, raspberry, and/or cherry flavors. In an embodiment, flavors may increase adherence by some patient populations such as pediatrics and may make chilled-air device enjoyable to use. In an embodiment, flavor droplets may be added to chilled-air inhaler device, for example through mouthpiece and/or through tube second end. In an embodiment, flavor may aid in reducing sugar cravings and dieting. Chilled-air permeable filling 124 may include an essential oil such as eucalyptus, menthol, peppermint, lemongrass, lavender, rosemary, and/or lemon oil. In an embodiment, flavor and/or essential oil may be contained within a porous material such as a pad which may be placed within hollow chamber 104 for example. Chilled-air permeable filling 124 may allow for air and/or water to percolate through it, allowing for air to be cooled and/or heated more rapidly. For example, chilled-air permeable filing such as water ice may be used as an air filtration device to chill air more rapidly. In yet another non-limiting example, chilled-air permeable filling 124 may contain water alone which may be used as an air filtration device to cool and/or warm air within hollow chamber 104 much more rapidly.

With continued reference to FIG. 1, at least an air-chilling surface 106 may include a heat-exchanging conduit 126. Heat-exchanging conduit 126 may include heat conductive material through which a cooled material flows. Heat-exchanging conduit 126 may be composed of a heat-conductive material. For instance, and without limitation, heat-exchanging conduit may be composed at least in part of ceramics, metal, fiber, and/or fired clay. Heat-exchanging conduit 126 may be flexible, and may have an interior and/or lumen mechanically isolated and separate from hollow chamber 104, such that liquid or gas moving through the interior and/or lumen is not in contact with material within hollow chamber 104; for instance, heat-exchanging conduit 126 may include tube or a length of tubing that runs or coils through hollow chamber 104, but does not open on hollow chamber 104, such that liquid flows from an entry point of the tube located outside the hollow chamber 104 to an exit point of the tube that is also located outside of the hollow chamber 104. Heat-exchanging conduit 126 may include a coil, such as without limitation a coil of tubing. Coil may have cooling properties when coil may be immersed in a liquid or gas, and/or when a liquid or gas flows through coil. Coil may exchange hot or warm air and generate cool and/or chilled air. Coil may be surrounded by ice, water, hot stones, and/or any other materials contained within hollow chamber 104. Environmental air may flow through coil. Coil may be composed of copper tubing for example and/or another material that may conduct heat easily. Coil may have any suitable shape, including without limitation a cylindrical shape having a length and diameter sized to fit within hollow chamber 108. Coil may include loops of coil forming a turn. Loops may increase the amount of coil material, thereby also increase surface area. Heat-exchanging conduit 126 may have structural variations to increase surface area and contact space between coil and air. For example, heat-exchanging conduit 126 may include vanes that may spread outwards from a coil, tubing, or other portion of heat-exchanging conduit into hollow chamber 104 to increase surface area. Heat-exchanging conduit 126 may include a pump which may assist in forcing liquid through a coil or other element of heat-exchanging conduit 126. A pump may include a device that may move fluids such as liquids and/or gases by mechanical force. In an embodiment, a pump may include mechanical operation and/or electric operation. A pump may include for example reciprocating positive displacement pumps, positive-displacement pumps, gear pumps, screw pumps, progressing cavity pump, roots-type pump, peristaltic pump, plunger pump, triplex-style plunger pumps, compressed-air-powdered double-diaphragm pump, rope pumps, impulse pumps, velocity pumps, gravity pumps, steam pumps, and/or valveless pumps. Heat-exchanging conduit 126 may be sized and shaped to provide a chilled material to a user. User may include any human being and/or animal. Heat-exchanging conduit 126 may be mounted in hollow chamber and may be configured to deliver cooled material. Heat-exchanging conduit 126 may include for example, a heat-exchanging surface. Heat-exchanging surface may be configured to accept a thermal material for chilling. Heat-exchanging surface may transfer heat from a thermal material to another material for cooling and/or chilling. For example, a thermal material such as water may be cooled by cooling coils. In an embodiment, heat-exchanging surface may have a thermal material configured to chill a liquid, such as water, and produce a cooled material such as water vapors and/or water ice. Cooled material may include a mist produced from water for example. In an embodiment, heat-exchanging conduit 126 may be configured to accept a material for heating. Heat exchanging surface may transfer heat to a material for heating. For example, heat-exchanging conduit may include a heated material such as hot rocks which may transfer heat to a material for heating and may produce a heated material configured to heat a substance, such as air for breathing. Heat-exchanging conduit 126 may include a delivery mechanism configured to interface with a user and deliver a cooled material from heat-exchanging conduit 126 to the user at mouthpiece 128. Heat-exchanging conduit 126 may be coupled to at least air-chilling surface 106 and may be configured to deliver a mist produced from water ice, and/or chilled air produced from water ice.

With continued reference to FIG. 1, chilled-air inhaler device includes a mouthpiece 128 connected to body 102. Mouthpiece may be located at second end of hollow chamber 120. Mouthpiece 128 provides a mechanism for delivering chilled-air to a user. Mouthpiece 128 includes mouthpiece opening 130 that a user may place at user's mouth, where placement "at" user's mouth as used herein includes placement at, in, on, and/or around user's mouth in such a way as to permit user to inhale chilled air; mouthpiece may alternatively or additionally be placed at user's nose and/or one or more nostrils of user. Mouthpiece opening 130 connects interior space of the hollow chamber to environmental air 132 located outside of the hollow chamber 104. Environmental air 132 located outside of the hollow chamber may include air located in the immediate exterior of chilled-air inhaler device. Environmental air 132 may include air in the immediate surrounding space located around the chilled-air inhaler device and/or a user. For example, environmental air 132 located outside of the hollow chamber 104 may include air in a bedroom that user stands in while using chilled-air inhaler device. When in use, mouthpiece may connect hollow chamber 104 to air in a user's respiratory system, for instance permitting the user to inhale air from the hollow chamber into the user's throat, nasal passages, bronchial tubes, and/or lungs. Mouthpiece opening 130 may be designed to fit in and/or around a user's mouth. In an embodiment, a user may place mouthpiece opening 130 in user's mouth and close user's lips around the mouthpiece 128. Mouthpiece opening 130 may provide a seal to the mouth of the user. Mouthpiece opening 130 may be composed of any suitable material and/or combination of materials. For instance, and without limitation, mouthpiece opening 130 may be composed at least in part of ethylene-vinyl acetate (EVA), thermoplastic, rubber, plastic, polyurethane, and/or laminated thermoplastic. Mouthpiece opening 130 may include a mask. Mask may not be placed in the mouth but rather may cover the mouth, nose, and/or entire face. Mask may be composed of any suitable material and/or combination of materials. For instance, and without limitation, mask may be composed of plastic, silicone, and/or rubber. Mask may provide a mechanism for delivering cooled-air to a user. Mask may include for example, an aerosol mask, an oxygen mask, a nebulizer mask, and/or an anesthesia mask, all of which are commonly known in the art.

With continued reference to FIG. 1, mouthpiece opening 130 may be connected to hollow chamber second end 120 by a flexible tube 134. Flexible tube 134 may extend beyond an outer surface of body 102. Flexible tube may include a flexible tube first opening 136, flexible tube second opening 138, and flexible tube body 140. Flexible tube 134 may include a hollow hose that may carry materials and/or fluids from one location to another. For example, flexible tube 134 may carry cooled air from air-chilling surface located at interior space of hollow chamber to mouthpiece located at second end of hollow chamber. Flexible tube 134 may be composed of any suitable material and/or combination of materials. For instance, and without limitation, flexible tube 134 may be composed of nylon, polyurethane, polyethylene, polyvinyl chloride (PVC), rubber, plastic, glass, polystyrene, polypropylene, metal, and/or aluminum. Flexible tube 134 includes a flexible tube first opening 136 connected to interior space of hollow chamber 104 and a flexible tube second opening 138 connected to mouthpiece opening 130. Flexible tube body 140 may have a cylindrical shape having a length to reach from interior space of the hollow chamber 104 to mouthpiece opening 130. Flexible tube body 140 may contain any fixed or bendable angle. Flexible tube 134 may have an accordion shape that may contain folding similar to the bellows of an accordion. Flexible tube 134 may have any fixed and/or varied cross-sectional shape. Flexible tube 134 may be composed of any type of tubing of any length. Flexible tube first opening 136 and/or flexible tube second opening 138 may be of a diameter necessary to connect with mouthpiece opening 130. In an embodiment, flexible tube first opening 136 may be equal in diameter to flexible tube second opening 138. In an embodiment, mouthpiece opening 130 may be disposable, whereby a user may detach mouthpiece opening 130 from flexible tube 134 and discard mouthpiece opening 130 after a single use and/or after a certain number of uses. In an embodiment, mouthpiece opening 130 may be permanently attached to flexible tube 134 and may not be discarded after use.

With continued reference to FIG. 1, chilled-air inhaler device includes an inlet 142. Inlet 142 may include an inlet opening 144 that connects interior space of the hollow chamber 104 to a source of air. Inlet 142 may include an indentation at the first end of the hollow chamber where the inlet opening 144 may be located. Inlet 142 may include a tube 146 having a first end and a second end. Tube may include a hollow hose that may carry materials and/or fluids from one location to another. For example, flexible tube may carry environmental air 132 located outside of the tube to inlet opening 144. Tube 146 may have a cylindrical shape. Tube may have any shape suitable for flexible tube 134 as described above. Tube 146 may be composed of any suitable material and/or combination of materials. For instance, and without limitation, tube 146 may be composed of material such as but not limited to nylon, polyurethane, polyethylene, polyvinyl chloride (PVC), rubber, plastic, glass, polystyrene, polypropylene, metal, and/or aluminum. Tube may have a first end 148 and second end 150. Tube first end 148 may be connected at inlet opening 144 located at the first end of the hollow chamber 136. Tube second end 150 may be open to environmental air 132 located outside of the tube. Environmental air 132 located outside of the tube may include air in the immediate surrounding space located around the chilled-air inhaler device and/or a user, as described in more detail above. Environmental air 132 may serve a source of air for chilled-air inhaler device. Tube 146 may have a cylindrical shape having a length to reach from inlet opening 144 at the interior space of the hollow chamber 104 to a source of air, such as environmental air located outside of the tube as described above. Tube first end 148 and/or tube second end 150 may be of a diameter necessary to connect with inlet opening 144. In an embodiment, tube first end 148 may be equal in diameter to tube second end 150.

With continued reference to FIG. 1, tube second end 150 may be connected to an external device 152. External device 152 may include a device that a user may connect to tube second end 150 independent and separate of chilled-air inhaler device. External device 152 may serve as a source of air for chilled-air inhaler device. External device 152 may connect to mouthpiece 128 at mouthpiece opening 130. For example, an external device 152 may connect at mouthpiece opening 130 by way of a y-junction, t-junction or the like; for instance, external device 152 may include a nebulizer that generates mist at mouthpiece 128 such as by way of a y-junction. In yet another example, a blower may connect at mouthpiece 128 and may draw air from hollow chamber first end 112, for instance and without limitation by means of the Venturi effect. In an embodiment, external device 152 may include for example, a blower. Blower may include a mechanical device that may create a current of air. Blower may include a fan, which may include a rotating arrangement of vanes and/or blades which act on air to produce currents of air. Fan may include for example, axial-flow, centrifugal, and/or cross-flow fans. An axial-flow fan may have blades that may force air to move parallel to the shaft about which the blades may rotate. A centrifugal fan may use kinetic energy of impellers to increase the volume of an air stream, which in turn may move impellers against resistance caused by ducts, dampers, and/or other components. A centrifugal fan may displace air by changing a direction of airflow. A centrifugal fan may be composed of a fan housing, impellers, inlet and outlet ducts, drive shaft, and a drive mechanism. Centrifugal fans may use centrifugal power supplied from the rotation of impellers to increase the kinetic energy of gases such as air. Cross-flow fans may include a vortex region, an eccentric vortex, and a paddling region. Cross-flow fan may have air flow through the fan. In an embodiment, external device 152 may blow hot air. For example, a fan and/or a blower may blow hot air which may be subsequently inhaled by a user. This may be of particular use for a user who is suffering from a cold and/or sinus infection where warm moist air may help to a greater extent than chilled-air. Hot air may also be of use for example in a frozen pond rescue where a child may have fallen through the ice and the body temperature needs to be raised rapidly. In an embodiment, user may alternate between chilled-air and/or hot air treatments.

Continuing to view FIG. 1, external device 152 may include a nebulizer. Nebulizer may include a device used to administer a substance in the form of a mist to be inhaled into a user's respiratory system, such as mist to be inhaled into bronchial passages or into lungs. Nebulizer may be used to administer medications, oxygen, and/or other substances. Nebulizers may use oxygen, compressed air, and/or ultrasonic power to break up medications, therapeutic substances, oxygen, and/or other substances into aerosol droplets that may be directly inhaled by a user. An aerosol may include a suspension of fine solid particles or liquid droplets dispersed in air and/or another gas. For example, a nebulizer may break up a medication such as albuterol or budesonide into aerosol droplets that may be directly inhaled by a user. In yet another non-limiting example, a nebulizer may break up a therapeutic substance such as menthol, or eucalyptus. Nebulizer may include mechanical and/or electrical nebulizers. Mechanical nebulizer may include a soft mist inhaler. A soft mist nebulizer may provide a metered dose of a substance to a user, as the liquid bottom of the nebulizer is rotated. In an embodiment, the nebulizer may be rotated by hand of a user. Soft mist nebulizer may include RESPIMAT as produced by Boehringer Ingelheim of Ingelheim, Germany. Electrical nebulizer may include a jet nebulizer, ultrasonic wave nebulizer, and/or vibrating mesh technology. Jet nebulizer may include a tubing connected to a compressor that may cause compressed air or oxygen to flow at a high velocity through a liquid medicine to turn it into an aerosol to be inhaled by a user. Jet nebulizer may include CIRCULAIRE II as produced by Westmed Inc., of Tucson Ariz., PARI LC PLUS as produced by Pan of Midlothian Va., PART LCD as produced by Pari of Midlothian Va., NEBUTECH as produced by Salter Labs of Arvin Calif., and/or AEROECLIPSE as produced by Monoghan/Trudell Medical international of Ontario, Canada, Ultrasonic wave nebulizer an include an electronic oscillator that may generate a high frequency ultrasonic wave, sufficient to create an aerosol. Ultrasonic wave nebulizer may include BEURER NEBULIZER IH30 as produced by Beurer of Neu-Ulm Germany. Vibrating mesh nebulizer may include a mesh membrane containing holes that may activate the top of a liquid reservoir and pressure out a mist containing aerosols through the holes. Vibrating mesh nebulizer may include AERONEB as produced by Aerogen of Galway, Ireland, EFLOW as produced by PARI of Starnberg, Germany, MICROAIR NE-U22 as produced by Omron of Bannockburn, Ill., I-NEB as produced by Philips Respironics of Newark, N.J., and AKITA as produced by Activaero of Gemunden Germany. External device 152 may include a spacer. A spacer may include a device that creates a temporary space to hold a substance to be inhaled with a nebulizer and/or mask. A spacer may assist in allowing a user to more precisely control activation of a substance to be inhaled and actual inhalation. In an embodiment, spacer may be attached to a mask. Mask may include any of the masks as described above. Spacer may include for example, AEROCHAMBER PLUS Z STAT as produced by Monaghan Medical of Plattsburgh, N.Y., MONAGHAN AEROCHAMBER MINI AEROSOL HOLDING CHAMBER as produced by Monaghan Medical of Plattsburgh, N.Y., MONAGHAN AEROTRACH PLUS ANTI STATIC VALVED HOLDING CHAMBER as produced by Monaghan Medical of Plattsburgh, N.Y., RESPIRONICS OPTI-CHAMBER DIAMOND ANTI-STATIC VALVED HOLDING CHAMBER as produced by Respironics of Murrysville, Pa., and/or HUDSON RCI POCKET CHAMBER as produced by Teleflex Incorporated of Wayne, Pa.

With continued reference to FIG. 1, chilled-air inhaler device 100 may include a handle 154 attached to an outer surface of body 102. Handle 154 may include a part designed to be grasped by a user hand. Handle 154 may include a hollow tube, such as hollow tube 146, connected to inlet 142. Tube may be located within the handle 154. In an embodiment, tube may be inserted through a hollow handle 154. In yet another non-limiting embodiment, tube may also be the handle 154; in other words, handle 154 may be hollow or may include a hollow portion, where the hollow handle and/or hollow portion acts as tube 146. In an embodiment, inlet 142 may include, be included in, or be attached to handle 154. In yet another non-limiting example, handle may be removeable to allow for chilled-air inhaler device 100 to be cleaned, shipped, and/or stored compactly for handling. In an embodiment, removable handle 154 may be able to fit inside hollow chamber 104.

With continued reference to FIG. 1, chilled-air inhaler device 100 may include a reclosable top 156 permitting access to hollow chamber 104. Reclosable top 156 may be any top that may be capable of being closed again after opening. Reclosable top 156 may be located between mouthpiece flexible tube 134 and second end of hollow chamber 120. Reclosable top 156 may have a cylindrical shape having a diameter size equal to body 102 diameter. Reclosable top 156 may have an oval shape having a diameter size equal to body 102 diameter. Reclosable top 156 may be derived from any material such as for example, silicone, hemp, and/or any green or recyclable material. Reclosable top 156 may include a twist-on top. Reclosable top 156 may be magnetic, may be a clip-on top, and/or may be open or closed by a hinge or locking mechanism. Reclosable top 156 may contain a silicone or gasket seal. Reclosable top 156 may be waterproof so that chilled air and/or water droplets do not break or corrode the space between reclosable top 156 and hollow chamber 104. In yet another non-limiting example, reclosable top 156 may include a screw-off top and/or a snap on/snap off top. For example, a user may un-twist reclosable top 156 to open and access hollow chamber 104 to load water ice for example. In yet another non-limiting example a user may un-twist reclosable top 156 to open and access hollow chamber 104 to wipe down and clean hollow chamber 104 after use. Hollow chamber 104 may also be accessed to drain any ice that may have melted and any accumulated liquids after use.

Figure 2:
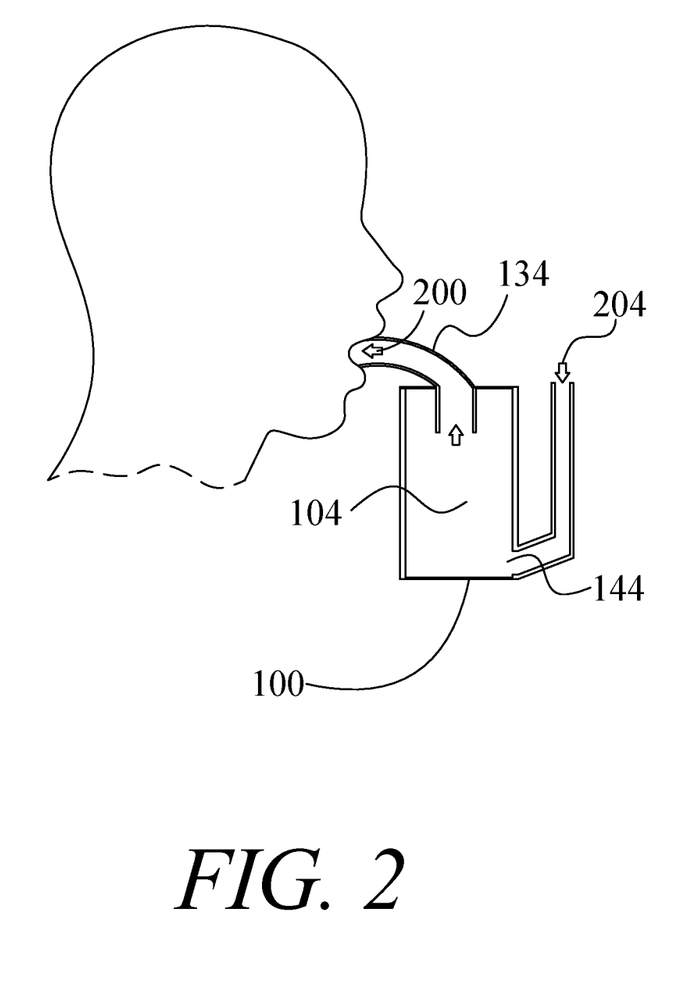
FIG. 2 illustrates a drawing of a user utilizing a chilled-air inhaler device for the alleviation of respiratory symptoms.

In operation, and referring now to FIG. 2, a user may place an end of tube 134 into the user's mouth, for instance by inserting mouthpiece opening 130 into the mouth. User may then draw breath in, allowing chilled air 200 to flow into the user's respiratory system, bronchia, and/or lungs. Chilled air may be impelled through chamber 104, and thus chilled, by suction induced by the user drawing breath, and/or by one or more mechanisms for impelling air as described above in reference to FIG. 1. Air to be chilled 204 may be drawn and/or forced in via inlet opening 144.

Figure 3:
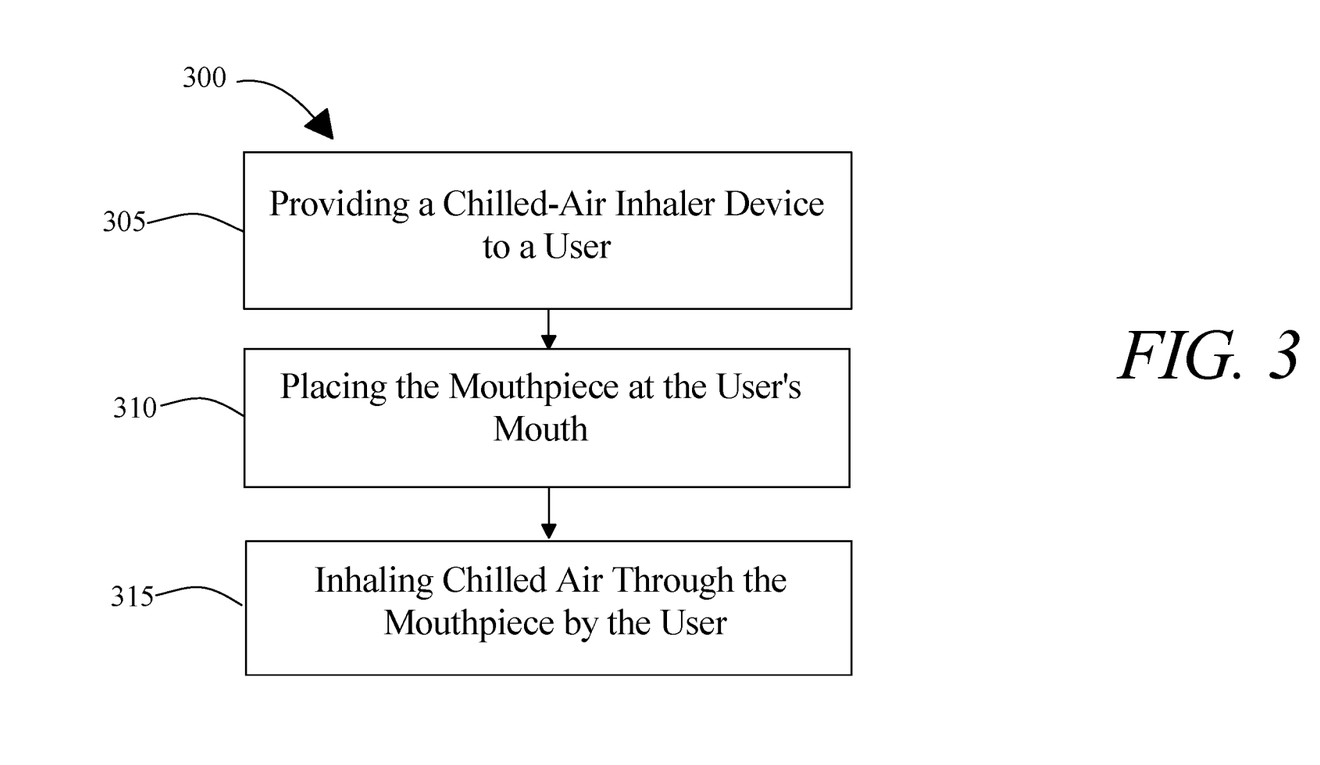
FIG. 3 is a block diagram of a method for using a chilled-air inhaler device for the alleviation of respiratory symptoms.

Referring now to FIG. 3, an exemplary method of using a chilled-air inhaler deliver for the alleviation of respiratory symptoms is illustrated. At step 305, a chilled-air inhaler device is provided to a user. Providing may include supplying chilled-air inhaler device to a user. Chilled-air inhaler device may be supplied by a doctor, for example to a user. In yet another non-limiting example, chilled-air inhaler device may be supplied by a friend and/or family member of a user. For example, a parent may provide chilled-air inhaler device to parent's child. In an embodiment, user may supply chilled-air inhaler device to user. For example, chilled-air inhaler device may be located in user's medicine cabinet at home, and user may locate and pick up chilled-air inhaler device from user's medicine cabinet when user needs to use chilled-air inhaler device. Providing chilled-air inhaler device may include preparing chilled-air inhaler device for use. Providing may include, as a non-limiting example, preparing the at least an air-chilling surface 106 by opening reclosable top and loading a chilled air-permeable surface 112 into hollow chamber 104. As a further non-limiting example, providing may include loading at least a piece of water ice into hollow chamber 104. In an embodiment, preparing chilled-air inhaler device for use may include switching on and/or loading external device 152. For example, nebulizer may need to be turned on and/or connected to chilled-air inhaler device. In yet another non-limiting example blower may need to be connected to chilled-air inhaler device and adequately adjusted to properly blow air into second end of inlet 150.

With continued reference to FIG. 3, at step 310 user places the mouthpiece at user's mouth. Placing mouthpiece at user's mouth may include closing user's lips around the mouthpiece. Placing mouthpiece may include properly placing mouthpiece opening 130 in user's mouth so that mouthpiece opening is fully enclosed by user's lips. This may assist in ensuring that user can inhale air through mouthpiece opening and directly into respiratory system of user. Mouthpiece opening that is not fully enclosed by user's lips may have to be adjusted to ensure air is not lost and that adequate amounts are able to reach respiratory system of user. In an embodiment, placing mouthpiece 128 in the user mouth may involve connecting a mask to mouthpiece 128. This may include for example placing a mask over a user's nose, lips, and/or face. For example, a young child who may not be able to breathe through mouthpiece 128 may wear a mask instead. Mask may include any of the masks as described above in reference to FIG. 1. Mouthpiece may be placed at any other entryway to user's respiratory system, including without limitation placement at a nostril or nose of user. A person other than user, such as a medical practitioner, family member, or the like, may place mouthpiece at user's mouth and/or at any other entryway to user's respiratory system.

With continued reference to FIG. 3, at step 315, user inhales air through the mouthpiece. Inhaling may include breathing in the chilled air through the mouthpiece. Inhaling may include drawing air into user's lungs through user's mouth, whereby the air that is drawn in is chilled air. After inhalation, the chilled air may be exhaled when the air is breathed out. In an embodiment, inhaling the air by the user may be done for a certain period of time, such as for example 3 to 5 seconds. In an embodiment, inhaling the air may be repeated by user if respiratory symptoms do not subside. For example, user may inhale repeatedly until coughing and/or wheezing slow down and/or dissipate entirely.

Embodiments of the disclosed device and method for using the device have several advantages over other devices used to control respiratory symptoms. In an embodiment, devices disclosed herein allow for relief of respiratory symptoms without the use of any pharmaceuticals. Devices disclosed herein may be used on a wide range of the human population, starting with the very young all the way up to the very old. Devices and methods disclosed herein may use inexpensive equipment that may be commonly found and available. Ice may be a common ingredient found in a user's freezer. In addition, embodiments of methods may allow for repeated use of chilled-air inhaler device with very little if any side effects and/or concerns about toxicity.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A chilled-air inhaler device for the alleviation of respiratory symptoms, the device comprising:
    a body, wherein:
        the body includes a hollow chamber;
        the hollow chamber has a first end and a second end; and
        the hollow chamber has an interior space containing at least an air-chilling surface, wherein:
            the at least an air-chilling surface comprises a chilled air-permeable filling allowing air to flow through the device from the first end of the hollow chamber to the second end of the hollow chamber;
            the chilled air-permeable filling includes water ice containing a first flavor to chill and flavor the air flowing through the device; and
            the interior space of the hollow chamber further contains a porous material, wherein the porous material contains a second flavor and an essential oil as further additives to the air flowing through the device;
    a mouthpiece connected to the body, wherein:
        the mouthpiece further comprises a mouthpiece opening connected to the second end of the hollow chamber; and
        the mouthpiece opening connects the interior space of the hollow chamber to environmental air located outside of the hollow chamber;
    a reclosable top permitting access to the hollow chamber, wherein the reclosable top is located between the mouthpiece and the second end of the hollow chamber, wherein the reclosable top includes a magnetic locking mechanism; and
    an inlet including an inlet opening located at the first end of the hollow chamber, wherein the inlet opening connects the interior space of the hollow chamber to a source of air, wherein:
        the inlet further comprises a tube having a first end and a second end;
        the first end of the tube is connected at the inlet opening; and
        the tube is configured in the form of a removable handle designed to be grasped by a user's hand, wherein the handle is sized to fit inside the hollow chamber.

2. The chilled-air inhaler device of claim 1 wherein the chilled air-permeable filling further comprises at least a piece of the water ice.

3. The chilled-air inhaler device of claim 1, wherein the air-chilling surface of claim 1 further comprises a heat-exchange conduit.

4. The chilled-air inhaler device of claim 3, wherein the heat-exchange conduit further comprises a coil.

5. The chilled-air inhaler device of claim 1, wherein the mouthpiece further comprises a mask.

6. The chilled-air inhaler device of claim 1, wherein the mouthpiece opening is connected to the second end of the hollow chamber by a flexible tube.

7. The chilled-air inhaler device of claim 6, wherein the flexible tube further comprises a first opening connected to the interior space of the hollow chamber and a second opening connected to the mouthpiece opening.

8. The chilled-air inhaler device of claim 1, wherein the handle is attached to an outer surface of the body.

9. The chilled-air inhaler device of claim 1, wherein the source of air is environmental air located outside of the body.

10. The chilled-air inhaler device of claim 1, wherein the source of air includes an external device.

11. The chilled-air inhaler device of claim 10, wherein the external device further comprises a blower.

12. The chilled-air inhaler device of claim 10, wherein the external device further comprises a nebulizer.

13. A method of using a chilled-air inhaler device for the alleviation of respiratory symptoms, the method comprising:
    providing the chilled-air inhaler device of claim 1 to a user;
    placing the mouthpiece at the user's mouth; and
    inducing the user to inhale chilled air through the mouthpiece.

14. The method of claim 13, wherein providing further comprises opening the reclosable top and loading the chilled air-permeable filling into the hollow chamber.

15. The method of claim 14, wherein loading the chilled air-permeable filling further comprises loading at least a piece of the water ice.

16. The chilled-air inhaler device of claim 1, wherein the device further comprises a lanyard connected to at least a connection point on an exterior surface of the body for allowing the body to be hung around a user's neck, wherein the lanyard includes a cord passing through the at least a connection point.

17. The chilled-air inhaler device of claim 16, wherein the device further comprises a plurality of feet extending from the body to support the body on a surface.

18. The chilled-air inhaler device of claim 1, wherein the essential oil comprises eucalyptus oil.

19. The chilled-air inhaler device of claim 1, wherein the essential oil comprises lemongrass oil.

* * * * *